(12) United States Patent
Beier et al.

(10) Patent No.: US 7,258,546 B2
(45) Date of Patent: Aug. 21, 2007

(54) MEDICAL OR DENTAL INSTRUMENT AND/OR SUPPLY UNIT AND/OR CARE UNIT AND/OR SYSTEM FOR THE MEDICAL OR DENTAL INSTRUMENT

(75) Inventors: Stefan Beier, Biberach (DE); Eugen Eibofner, Biberach-Mettenberg (DE); Hans Heckenberger, Biberach (DE); Ernst Strohmaier, Bad Schussenried (DE); Armin Imhof, Biberach (DE)

(73) Assignee: Kaltenbach & Voigt GmbH & Co. KG, Biberach (DE)

( * ) Notice: Subject to any disclaimer, the term of this patent is extended or adjusted under 35 U.S.C. 154(b) by 221 days.

(21) Appl. No.: 10/479,861

(22) PCT Filed: Jun. 4, 2002

(86) PCT No.: PCT/EP02/06136

§ 371 (c)(1),
(2), (4) Date: Apr. 27, 2004

(87) PCT Pub. No.: WO02/098315

PCT Pub. Date: Dec. 12, 2002

(65) Prior Publication Data

US 2004/0209223 A1    Oct. 21, 2004

(30) Foreign Application Priority Data

Jun. 7, 2001    (DE) ................ 101 27 772

(51) Int. Cl.
*A61C 1/00* (2006.01)
(52) U.S. Cl. .................. 433/27; 433/99; 433/104; 600/117
(58) Field of Classification Search ............ 433/98, 433/99, 27, 103, 104; 600/117
See application file for complete search history.

(56) References Cited

U.S. PATENT DOCUMENTS

| 4,862,872 A | * | 9/1989 | Yabe et al. ............. 600/133 |
| 5,400,267 A | * | 3/1995 | Denen et al. ............ 702/59 |
| 5,807,521 A | | 9/1998 | Franetzki ............... 422/20 |
| 6,017,354 A | * | 1/2000 | Culp et al. ............. 606/170 |
| 6,092,722 A | | 7/2000 | Heinrichs et al. ........ 235/375 |
| 6,117,285 A | | 9/2000 | Welch et al. ............ 204/237 |
| 6,217,329 B1 | * | 4/2001 | Eibofner et al. ......... 433/104 |

(Continued)

FOREIGN PATENT DOCUMENTS

DE    37 26 262 A1    2/1989

(Continued)

OTHER PUBLICATIONS

International Search Report in PCT/EP02/06136 dated Dec. 3, 2002.

(Continued)

*Primary Examiner*—Ralph A. Lewis
(74) *Attorney, Agent, or Firm*—Marshall, Gerstein & Borun LLP

(57) ABSTRACT

The invention relates to a medical or dental-medical instrument (2) having a memory element (10p) for identification and/or operational parameter data. IN order to extend the range of possible applications of the instrument, the memory element (10p) is constituted for the overwriting of the data by other data.

12 Claims, 4 Drawing Sheets

U.S. PATENT DOCUMENTS

Figure 6:
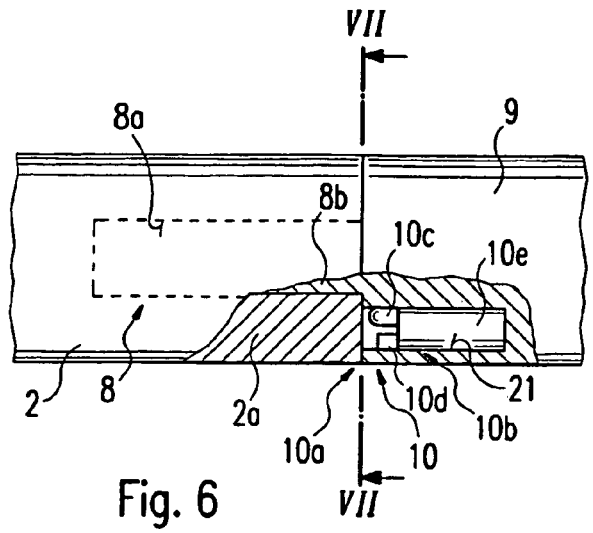

| | | | |
|---|---|---|---|
| 6,436,032 B1 * | 8/2002 | Eto et al. | 600/117 |
| 6,712,756 B1 * | 3/2004 | Kura et al. | 600/118 |
| 2001/0041825 A1 * | 11/2001 | Shibata et al. | 600/118 |
| 2002/0129454 A1 * | 9/2002 | Hilscher et al. | 15/22.1 |
| 2005/0100867 A1 * | 5/2005 | Hilscher et al. | 433/216 |

FOREIGN PATENT DOCUMENTS

| | | |
|---|---|---|
| DE | 42 20 522 A1 | 1/1994 |
| DE | 44 10 276 A1 | 9/1995 |
| DE | 197 29 177 A1 | 1/1999 |
| DE | 199 13 962 A1 | 10/2000 |
| WO | WO98/06338 | 2/1998 |

OTHER PUBLICATIONS

International Preliminary Examination Report in PCT/EP02/06136 dated Sep. 29, 2003.

* cited by examiner

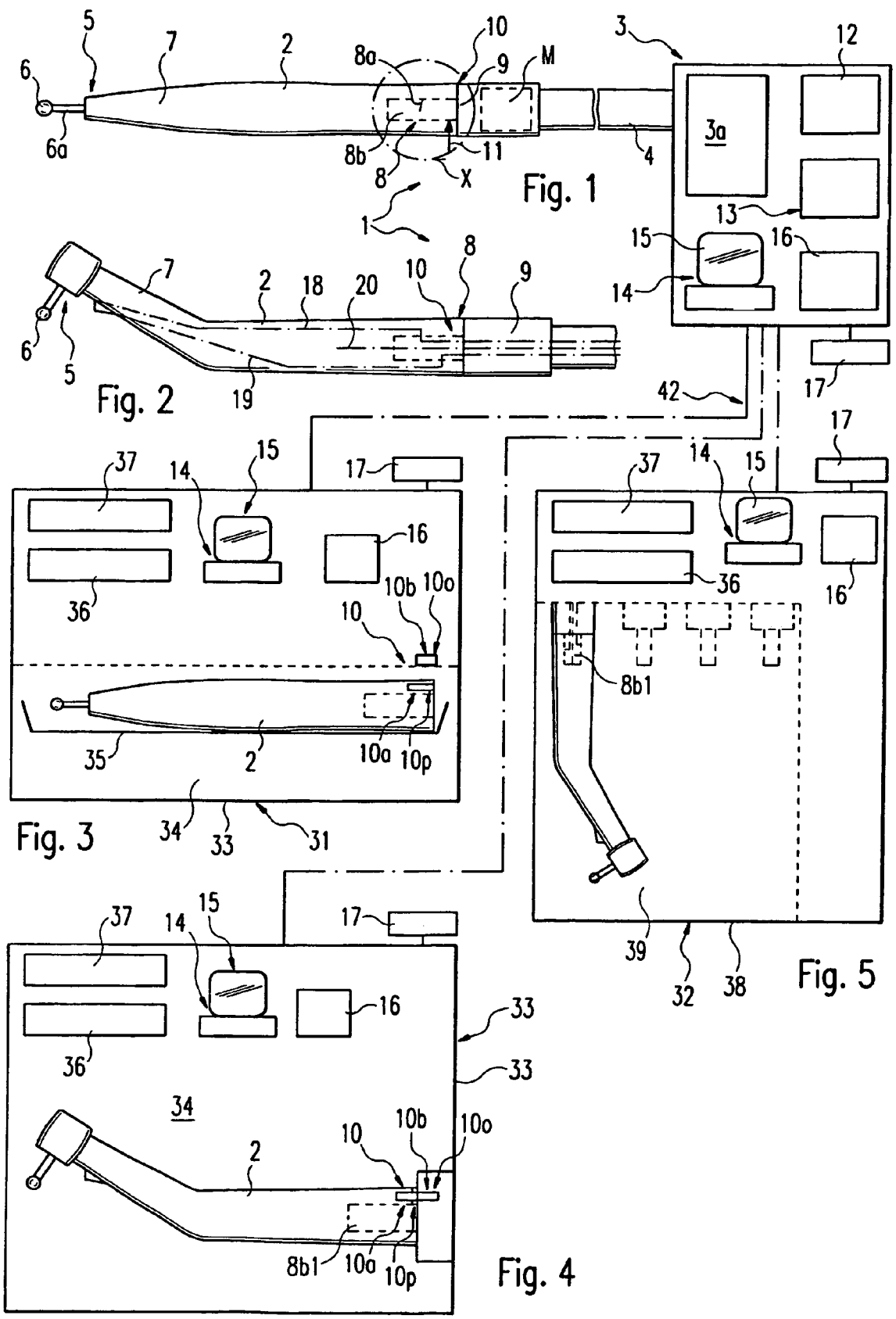

MEDICAL OR DENTAL INSTRUMENT AND/OR SUPPLY UNIT AND/OR CARE UNIT AND/OR SYSTEM FOR THE MEDICAL OR DENTAL INSTRUMENT

This is the U.S. national phase of International Application No. PCT/EP02/06136 filed Jun. 4, 2002, the entire disclosure of which is incorporated herein by reference.

The invention relates to a medical or dental-medical instrument or a supply apparatus and/or a maintenance apparatus or a system for medical or dental-medical instruments.

A medical or dental-medical instrument is an object which is put to use for working the human or animal body or parts (prostheses) thereof, and thereby comes into contact with the body and thereby may be be soiled and/or contaminated with disease causing agents. This in particular then when the instrument comes into contact with a secretion or a fluid of the body. It is therefore necessary after the working of one patient or before the working of a next patient, to clean and/or to disinfect/sterilise the instrument. The respective measure concerned is dependent on the one hand on how intensive the contact of the instrument with the body was and on the other hand which working measure was carried out.

The configuration and functioning of an instrument of the kind concerned can, moreover, differ widely. In particular with an instrument as mentioned above, the tool of which is moved by means of a drive, there is needed at certain intervals a mechanical servicing of the at least one instrument in order to maintain its capability for functioning and to avoid wear and disruptions to functioning. There are instruments with which, independently of whether they have been soiled and/or contaminated in functional operation, there is a rule that the instrument be serviced at certain intervals, e.g. after certain numbers of operating hours. The above-indicated measures for the maintenance of the readiness for use of the at least one instrument are designated in the following by the term "maintenance". Thus, for an instrument of the kind concerned, there is a working phase, in which it acts on the body at least for some periods of time, and a maintenance phase, in which the instruments acted upon for maintaining its readiness for use.

In the working phase, the instrument is connected with a medical or dental-medical supply apparatus. In accordance with today's standard, the supply apparatus has an electronic control device from which a bendable or flexible supply line extends, with which the instrument is connected by means of a releasable coupling. The instrument or its tool is supplied or controlled for its functioning through the supply line from the supply apparatus. Here there may be involved the delivery of drive energy and/or working media.

There may be associated with the supply apparatus only one or a plurality of different instruments, which are selectively connectable with the supply line by means of the coupling. Here, depending on the kind of instrument, different drive media may be present or supplied. A supply apparatus of this kind is described for example in DE 4 410 276 A1.

In DE 42 20 522 A1 there is described a system for making recognisable various consumer loads, for example dental instruments, with respect to an energy supply unit belonging to a dental treatment station, with a coding means provided on a supply line for the identification of an instrument associated with the supply line and with an evaluation circuit belonging to the energy supply unit which is connected by means of electrical connecting lines with the coding means. The electrical connection lines extend through the supply line.

From DE 19 729 177 A1 there can be understood a medical supply apparatus with which, with the aid of an electronic control device, an instrument with a tool couplable to a drive motor can be supplied and controlled. There are stored in the control apparatus, by the manufacturer, fixedly predetermined operational programs for the operation of certain instruments and tools. Further, user specific operational programs can be produced. Moreover, with the aid of a selection button, a setting mode can be called up in which the user can arbitrarily intervene in the operational procedure and arbitrarily alter the operational parameters.

In DE 199 13 962 A1 there is described a maintenance device for dental handpieces, having a housing which encloses a maintenance chamber. There is arranged in the maintenance chamber at least one coupling part for receiving the one end of an instrument, a maintenance delivery line extending to the coupling part. For the purpose of ensuring a simple configuration and a reliable functioning there is associated with the coupling part a sensor which is activated by the instrument in its maintenance disposition, for the purpose of issuing a signal to a control device of a maintenance apparatus, in response to which the control device controls the delivery system for maintenance medium.

A coding on an instrument of the kind concerned here may contain identification and/or operational parameter data and thus represents a memory element for such data which upon a coupling of the instrument with a medical or dental-medical supply apparatus can be called up by the apparatus and can be used for controlling the supply of the instrument.

The invention is based on the object of, with an instrument with accordance with the preamble of claim 1, broadening the range of possible applications.

With an instrument in accordance with the invention, the memory element is constituted for the overwriting of the data by other data. Through this it is possible to alter the data memory on the instrument. Consequently, the instrument can be used as data carrier for the altered data, from which substantial advantages arise. On the one hand the instrument is, at least for the period of time in which it is separated from the apparatus, independent of the data memory of the apparatus. Further, through a selective coupling with a plurality of apparatuses, the instrument can transfer the altered data to the respective apparatus concerned, so that a data transfer directly between the apparatuses is not needed. Beyond this, the invention also leads to the advantage that the instrument, due to the alterability of its data, can not only be adapted to different data but is also suitable to collect data, e.g. in operational phases following one another. Here, there can be written into the memory at least one parameter of a previous operational phase and it can be read out for control of the next operational phase. Dependencies between operational phases can be created, and a further operational phase then carried out only if the previous operational phase has been carried out. A data query in this regard can be called up upon coupling of the instrument with an apparatus for carrying out the further operational phase. This is in particularly important if operational phases should or must only be carried out if the previous operational phase has been carried out. This requirement arises in the maintenance and/or servicing of the instrument. Furthermore, the instrument is suitable for a continuing registration of its data, so that the operational usage of the instrument can be understood.

Further, the invention is based on the object, with a supply apparatus, in one embodiment of improving or broadening the carriage of data.

With a supply apparatus in accordance with one embodiment of the invention, the data receiver or a reading device is also a data transmitter for the transfer of data to the memory element. Through this, data can be issued through the supply line and the data store of the supply apparatus can be relieved from demands at least for the time for which the instrument is decoupled from the supply apparatus, since data relating to the memory element can be given to the memory element. Beyond this, this configuration in accordance with the invention leads to a substantial simplification of the supply apparatus because in the case of the presence of a plurality of supply apparatuses, with which the instrument can selectively be coupled, no direct data line between the apparatuses is needed. The carriage of data can namely be assumed by the instrument with its data transferred in each case from the apparatus. When the instrument is coupled with a second apparatus, the second apparatus can call up the data from the instrument so that a direct data line between the apparatuses is not needed.

The invention is further based on the object of improving and/or simplifying the functioning and/or control of a maintenance apparatus one embodiment.

The maintenance apparatus of one embodiment has a reading device for reading out identification and/or operational parameter data stored in the instrument. Through this, the maintenance apparatus can be controlled in dependence upon identification and/or operational parameter data. Thereby there takes place an automatic adaptation of the functioning or control of the maintenance apparatus to the respectively read out identification and/or operational parameters. Further, this configuration also leads to a substantial simplification of the maintenance apparatus, because in a functionally connected system with at least one further apparatus there is needed no direct networking between the apparatuses, since the data carriage can be effected via the instrument and called up upon the coupling of the instrument with the apparatus concerned.

The invention further has the object of so configuring a system for the usage and maintenance of a medical or dental-medical instrument that a better or simple functioning or controlling of the maintenance apparatus is possible.

With the system according to one embodiment, the maintenance apparatus is also connected with the computer, whereby it stands in data exchange also with this computer. Through this, the maintenance apparatus can be controlled from an available computer and can be simplified, since the maintenance apparatus does not need its own controller means. Beyond this, control data can be put to use which is already stored in the computer of the supply apparatus, since the supply apparatus is also set up for the supply of the instrument, and thus for the control of the maintenance apparatus there can be put to use the available identification and/or operational parameters.

The invention further has the object of improving a system for the functional operation of at least one medical or dental-medical instrument with two medical or dental-medical apparatuses.

This object is achieved by means of the features of one embodiment. With a system according to one embodiment, there are provided registration means, by means of which the development or the desired value and/or actual value of at least one operational parameter of at least one operational phase is or are registerable. Through this, there can be recorded and understood and represented, and if applicable documented, selectively data and/or functional sequences of the system concerning the actual operation of the instrument. Through this an investigation of the operational sequence is substantially simplified.

It is particularly advantageous to detect and to register the actual value of the at least one operational parameter or feature. This is inter alia advantageous for the monitoring and/or improvement of safety, because the actually attained actual value is determined and can be registered, rather than a value set by the manufacturer or a user-specific value, for example a tool speed of rotation in the case of a treatment device, or a sterilisation temperature in the case of a steriliser. Thus, there is taken into consideration the parameter value which is important for technical safety reasons with regard to a working procedure and/or maintenance procedure. This is, for example, clear in the case of a maintenance device in the form of a steriliser. If the steriliser does not attain the predetermined desired value of the sterilisation temperature in the maintenance phase this can be detected or determined with the system in accordance with the invention and thus understood and if applicable also documented. This is particularly important in relation to the furnishing of proof or evidence, for example with regard to warranty claims and/or fulfillment.

The registration means may be associated with at least one apparatus and/or the instrument, and be provided by means of an electronic memory or a memory chip, to which the desired value or values and/or actual values of the parameter or parameters, or of other working-specific and/or maintenance-specific information, can be transferred and stored in the form of data, for example can be stored during the working phase and/or the maintenance phase.

The invention also makes it possible to improve safety in that an incorrect usage of procedures and/or an incorrect maintenance procedure is avoided. For this purpose, a control means connected with the registration means can be so constituted that a use of an instrument which is not prepared or insufficiently prepared, in particular insufficiently sterilised, is avoided by means of a fault report or blocking of functioning, or the like. In corresponding manner it is also possible to avoid a maintenance procedure for which the instrument is not suitable, for example a sterilisation ban, for example by indication or blocking.

With the invention, the transfer of the data between the memory and control means of at least one apparatus and at least one instrument can be transferred by means of wireless remote control (wireless transfer path, e.g. radio or infrared transfer path) or by means of electrical or optical lines.

Features are contained in subclaims which improve the configuration and functioning of the data line in the region of a coupling for the instrument, and lead to compact constructions.

Below, advantageous configurations of the invention will be explained in more detail with reference to preferred exemplary embodiments and drawings. There is shown:

FIG. 1 a medical or dental-medical working apparatus in accordance with the invention, in a schematic side view;

FIG. 2 a medical or dental-medical instrument as part of multiple purpose equipment for the working apparatus;

FIG. 3 a first maintenance apparatus in the form of a sterilizer, in a schematic side view;

FIG. 4 a first maintenance apparatus in the form of a sterilizer, in a modified configuration, in a schematic side view;

FIG. 5 a second maintenance apparatus in the form of a cleaning and/or lubricating apparatus, in a schematic side view;

FIG. 6 an exemplary embodiment of the detail designated in

Figure 7:
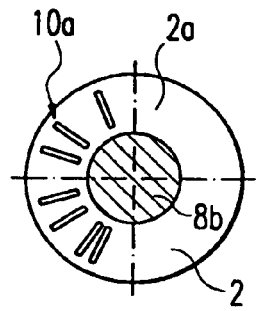
Figure 9:
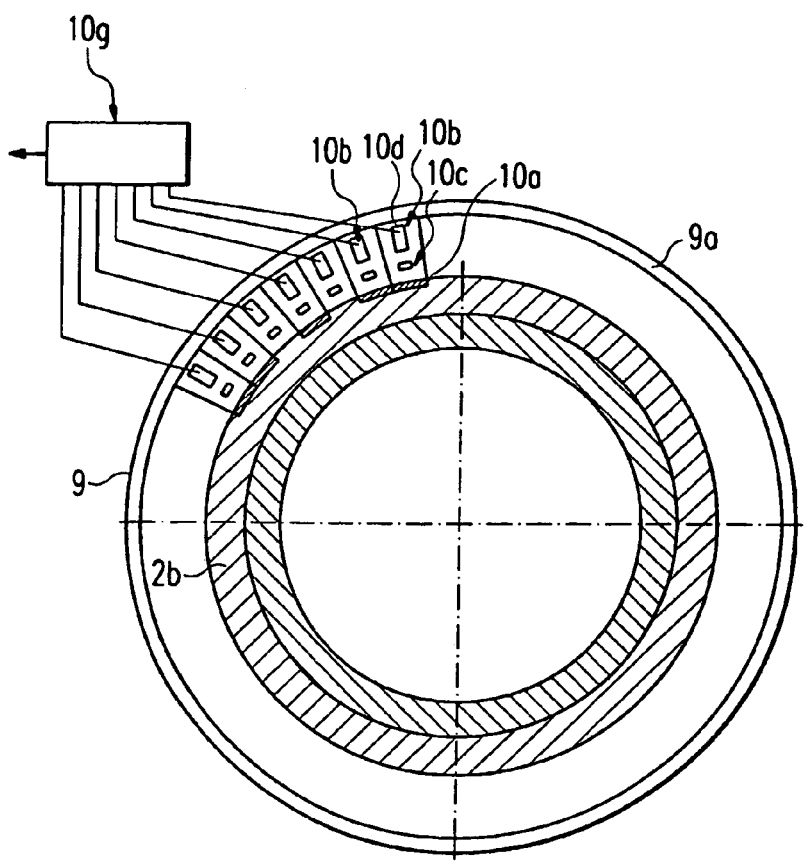
Figure 8:
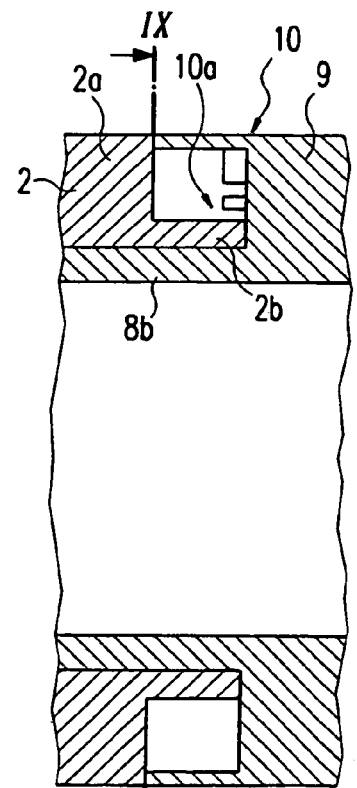
Figure 10:
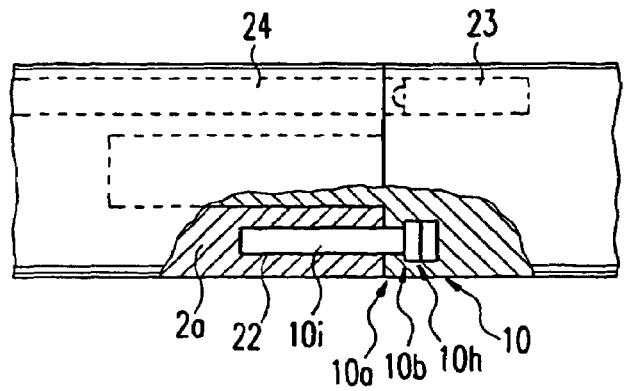
Figure 11:
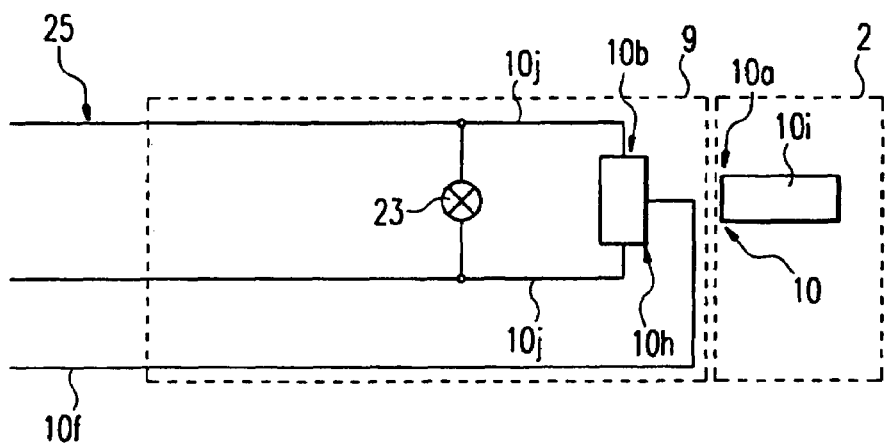
Figure 15:
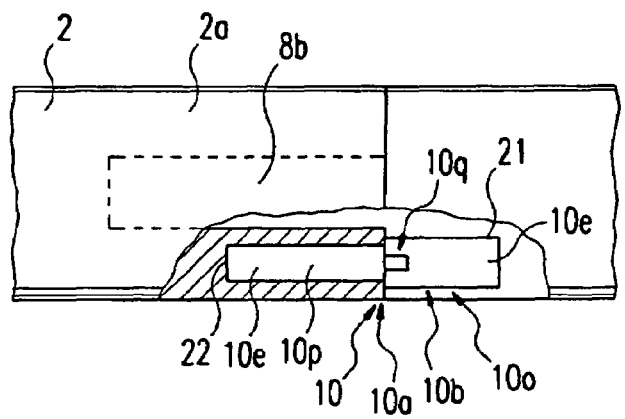
Figure 16:
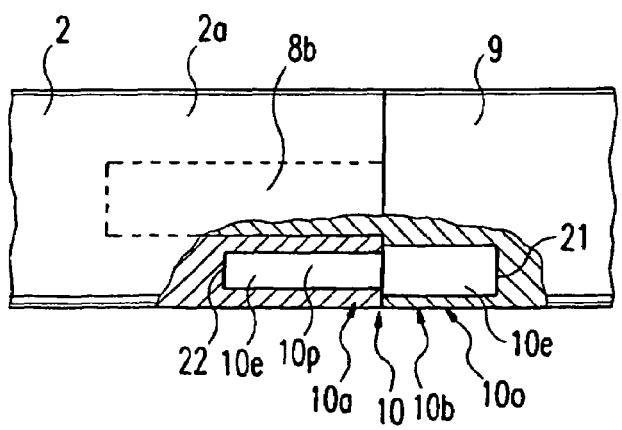
Figure 12:
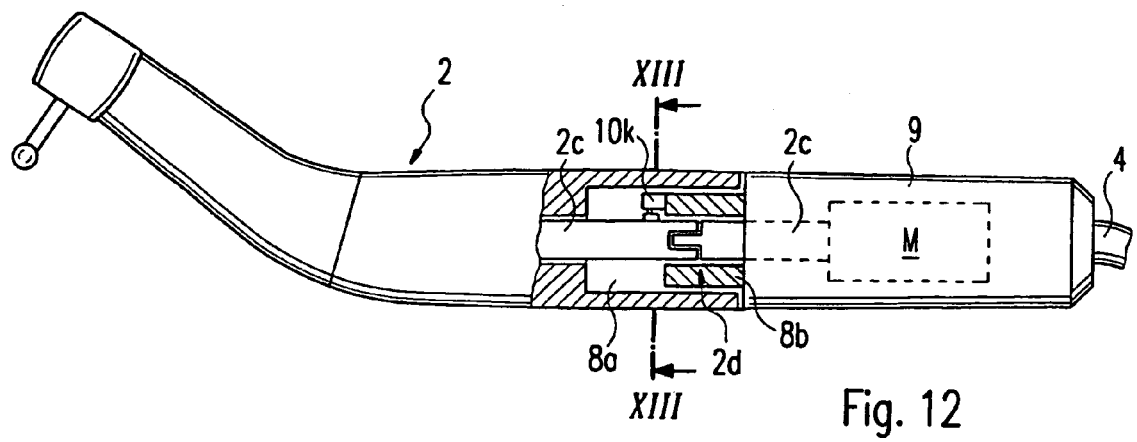
Figure 13:
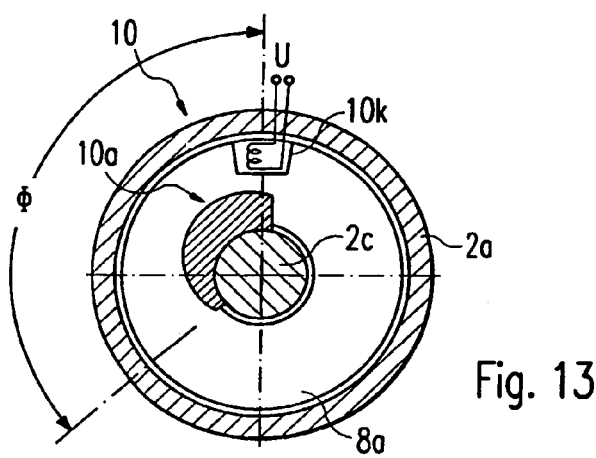
Figure 14A:
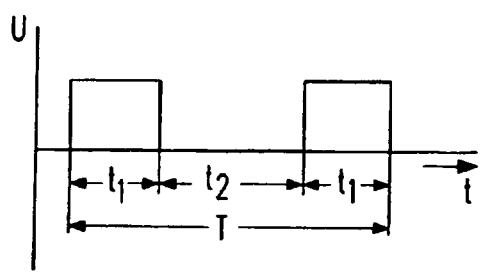
Figure 14B:
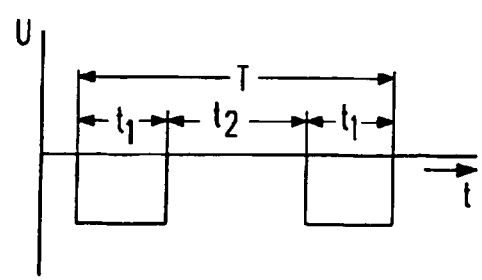

FIG. 1 by X, in a representation to an enlarged scale;

FIG. 7 the detail X in a modified configuration;

FIG. 8 the detail X in a further modified configuration;

FIG. 9 the section IX-IX in FIG. 8;

FIG. 10 the detail X in a further modified configuration;

FIG. 11 the detail X in a modified configuration, in a side view;

FIG. 12 an instrument having the detail X, in a further modified configuration;

FIG. 13 the section XIII-XIII in FIG. 12;

FIGS. 14a and 14b the temporal development of the voltages generated in the exemplary embodiment according to FIGS. 12 and 13;

FIG. 15 the detail X in a further modified configuration;

FIG. 16 the detail X in a further modified configuration.

The main parts of the working device or working apparatus, designated in its entirety by 1, are an instrument 2 for the working of the human or animal body or parts (prostheses) thereof, a supply apparatus 3 for supplying the instrument 2 with energy and with drive and operating media such as electric current, light, water and air, a bendable or flexible supply line 4, which is connected with the supply apparatus 3 at its rearward end and its forward free end is connected with the instrument 2 by means of a releasable coupling. With the exemplary embodiment according to FIG. 1, the instrument 2 is a material removing instrument 2, for example drill instrument, which has in its forward region a holder or mounting device 5 in which a tool 6 is releasably inserted with a tool shaft 6a. The instrument 2 is of elongate or rod-like structural form and extends for example, in accordance with FIG. 1, straight. In the case of the present exemplary embodiment, the instrument is a so-called handpiece 7, which is connected by means of a releasable coupling 8, in particular a plug-in coupling or a plug-in/turn coupling with a so-called connection part 9 which is connected non-releasably or releasably, for example by means of a screw connection, with the supply line 4. The coupling 8 is preferably formed by means of a coupling recess 8a in the one coupling part and a coupling pin 8b, matching the coupling recess 8 with play for movement, on the other coupling part. Preferably the coupling recess 8a is arranged in the rearward end region of the handpiece, whereby it opens out rearwardly, and the coupling pin 8b projects from the connection part 9 forwardly. The coupling recess 8a and the coupling pin 8b are preferably formed round, so that a relative rotatability between these parts is ensured which facilitates the handling of the instrument 2 or the handpiece 7. The plug-in coupling or plug-in/turn coupling 8 has associated therewith a releasable latching device 11 which preferably can be manually overcome and thus upon plugging together self-actingly comes into function and which can be brought out of function by overcoming with a manual exercise of pulling force. Such a latching device 11 is preferably formed by means of a latching edge on the one coupling part and a latching element on the other coupling part which is moveable, against an elastic return force, out of a coupling position engaging behind the latching edge. Through this, the latching device 11 self-actingly snaps in upon plugging together of the coupling parts, and for release it can be manually overcome as described above.

The supply apparatus 3 has for its control and functioning a switch table 12 for the setting of desired functions, an electronic control device 13 having an evaluation circuit for reading out the read data and for the control and regulation of the functions, whereby a computer 14 may be integrated for the control or regulation, in particular a PC having a screen 15 for the display of operational parameters and data of the instrument 2 or tool 6 and of the supply apparatus 3, and associated functions and conditions, and a registration device 16 and a printer 17 for the registration or recording of the above-mentioned data or information.

For carrying out different types of work there may be associated with the working device 1 a plurality of instruments 2, as is per se known. FIG. 2 shows by way of example an instrument 2 in the form of a so-called angled piece. The instrument or instruments 2 may thus involve such different constructions and functions as are in each case appropriately formed with regard to the coupling 8, so that they can be selectively coupled onto the connection part 9 and are exchangeable. There may be involved an instrument having a drive shaft axially extending thereon, which is rotatable by means of a motor M, for example an electric motor, arranged in the connection part 9 and which stands in driving connection with the tool 6. The tool 6 may be also be driveable by means of a compressed air turbine arranged in the forward end region of the instrument 2, which turbine is supplied by means of a compressed air delivery line and discharge line extending from the supply apparatus 3 and longitudinally through the supply line 4, the connection part 9 and the instrument 2.

For the delivery of operating media or working media the instrument may have an air line, a water line or a spray line, which in a manner known per se emerge in the forward end region of the instrument 2 and are directed towards the work site. The instrument 2 may also have an illumination device having a longitudinally extending light conductor or a longitudinally extending electric line with lamp, which extend to a light exit arranged in the forward end region of the instrument 2. For the supply of the above-described devices there serve so-called media lines which extend from a supply unit 3a of the supply apparatus 3 through the supply line 4 to the associated consumer load in the connection part 9 or in the instrument 2. If a turn/plug-in coupling is provided, a media line can in particular pass through this coaxially in a sealed manner and/or a plurality of media lines can pass through the cylindrical dividing joint between the coupling pin 8a and the coupling recess 8b in a sealed manner in a Z-form, as is per se known. For making more clear these per se known relationships there are schematically illustrated in FIG. 1 by way of example three media lines 18, 19, 20 for water, compressed air and light, which pass through the coupling 8 co-axially or Z-like.

For the setting of different working or operational programs, the working device 1 has at least two program levels. In a first program level, the user can select between a plurality of treatment or operational programs predetermined by the manufacturer or in the workshop. In a second program level, the user can select between a plurality of user-specifically created operational programs. After selection of one of the operational programs, the control device 13 controls the instrument 2 or the tool 6 in dependence upon the operational parameter information or data corresponding to the selected operational program. The user can select as desired between the user-specific stored operational programs and the operational programs predetermined by the manufacturer.

The operational parameter data associated with each operational program contains information concerning an instrument 2 to be selected and its drive and/or working specific data, e.g. speed of rotation, transmission ratio, efficiency, operating media, and operating media quantity etc.

The registration device 16 makes it possible to register and call up, for example for the purpose of display on the screen 15 or through printing out with the printer 17, desired operational and user-specific data and information going beyond the current operation time.

For the identification of the instruments 2 these have in the region of the coupling part of the instrument 2 a coding 10a which is readable by a reading device 10b which is arranged in the region of the other coupling part on the connection part 9 or on the supply line 4 and is connected by means of at least one associated data line with the control device 13.

The registration device 16 is preferably set up, in the case of data which may be variable in functional operation, to register not only the set desired value, for example set by the user, but also the actually attained actual value. Here there may be involved for example a maximum speed of rotation, which may be different depending upon load and power. The registration of the actual value makes it possible to record the actual situation, to call up and display the situation, in order for example subsequently to clarify and assess operations.

The identification device designated by 10 may be for example optical, electromagnetic or inductively effective. In the case of a plug-in/turn coupling 8 having a coupling recess 8a and a coupling pin 8b it is advantageous to arrange the identification device to both sides of the cylindrical or radial dividing joint of the coupling 8. The coding 10a may be arranged in the case of the exemplary embodiment in or on the sleeve wall 2a of the instrument 2 surrounding the coupling recess 8a, whereby the reading device 10b may be arranged in the coupling pin 8b or in the connection part 9 lying opposite to the sleeve wall 2a. In the first case, the working direction of the identification device 10 is radial, whereby the data of the reading device 10b is accessible from the outer surface in the coupling pin 8b, while in the second case the reading device 10b is arranged in the axial projection region of the sleeve wall 2a and with the data accessible from the annular step surface on the connection part 9.

In the case of the exemplary embodiment according to FIG. 6, in which the same or similar parts are provided with the same reference signs, there is an optical identification device 10 having a coding 10a, for example in the form of a pattern code, in particular a bar code, on a rear surface, here the rear surface of the sleeve wall 2a, and a reading device 10b behind the radial dividing joint in the connection part 9. This reading device 10b has a light source 10c, for example formed by means of a light emitting diode, and a photocell sensor 10d which are arranged or embedded preferably in a common in particular cylindrical carrier 10e which is fixedly placed in a recess 21 which opens out at the annular step at the radial dividing surface. The pattern code (bright and dark areas) is preferably formed by means of radial stripes between which there are included different angles, as is shown in FIG. 7. The reading direction runs axially or axis parallel.

In the case of the exemplary embodiment according to FIGS. 8 and 9, in which the same or similar parts are provided with the same reference signs, the reading direction of the reading device 10b is radially directed, here radially inwardly. In the case of the exemplary embodiment, there are arranged a plurality of photocell sensors 10d next to one another, in the circumferential direction with regard to the coding 10a, and radially outwardly. The coding 10a is formed by means of a light-dark marking on an outer circumferential or segment surface, in particular by a bar code. As FIG. 9 shows, the coding 10a and the reading device 10b are arranged on parts of the coupling parts lying radially opposite one another. Here, the coding 10a may be arranged on an outer surface of an inner shoulder 2b on the instrument 2 which is engaged over by the reading device 10b. The photocells, preferably present in a plurality, can on the one hand be arranged on a forwardly directed end face of the connection part 9 and on the other hand brought together in a sensor ring segment. A free space receiving the reading devices 10b may be covered over by a projecting sleeve extension 9a of the connection part 9. A parallel-serial converter or evaluation circuit is designated by 10g.

The exemplary embodiment according to FIGS. 9 and 10 shows an identification device 10 having an in particular magnetic sensor 10h, for example a Hall sensor or a field plate, in appropriate arrangement behind the radial dividing joint of the connection part 9. A magnet 10i is arranged in the sleeve wall 2a opposite to the sensor 10h in a rearwardly opening recess 22. FIG. 11 shows schematically the arrangement and the electrical connection of the sensor 10h in the case in which an illuminating device having a lamp 23 is present, which in the case of the exemplary embodiment is arranged in the connection part 9 offset in the circumferential direction with regard to the sensor 10h, and feeds light into a light conductor 24 extending forwardly in the sleeve wall 2a and arranged in the instrument 2 opposite to the lamp 23. The sensor 10a is connected through electrical line sections 10j to the current circuit 25 of the lamp 23. The coding 10a can be constituted in this exemplary embodiment in that different instruments have magnets 10i having different strengths of electromagnetic fields and/or the air gap spacings between the Hall sensor 10h and the magnets 10i is in each case different in the coupled condition. Through this, there are produced different electrical potentials in the sensor 10h which are delivered through a signal line of the electronic control device 13, which extends from the sensor 10h through the connection part 9 and the supply line 4 rearwardly to the electronic control device 13, for the setting of the desired operational data.

In the case of the exemplary embodiment according to FIGS. 12 to 14, the identification device 10 for an instrument 2 is provided in that in the region of the coupling 8 there is mounted a rotary part, which in the case of the exemplary embodiment is a drive shaft 2c which is rotatably mounted in a drive channel of the instrument 2. The rearward end of the drive shaft 2c is coupled by means of a plug-in coupling 2d with a drive shaft section 9a rotatably mounted in the connection part 9, which drive shaft section may be for example the drive shaft of the motor M. With this configuration there is provided a sensor 10k which is held in the connection part 9, at the end face side of the coupling pin 8b. On the drive shaft 2c of the instrument 2 there is located a sender element 10a of ferromagnetic material which extends over an angle Φ and has a height which reduces over the angle Φ. It has—seen in an evolved view—the form of a ramp. The sender element 10a passes the sensor 10k upon rotation the drive shaft 2c. The sensor 10k is for example a coil in which the sender element 10a, moving past the coil, generates a potential U dependent upon the speed of rotation and the direction of rotation of the drive 2c.

There is now possible a coding of the instrument 2 through selection of the starting and finishing height of the sender element 2a and/or through selection of the angle Φ over which the sender element extends, in other words, a coding is possible through the selection of a certain ramp form.

In FIGS. 14a and 14b there are illustrated the output signals of the sensor element 10k, as potential U in dependence upon time. Upon rotation of the drive shaft 2c in FIG. 13 there arise potential pulses.

In FIG. 14a, the potential pulses are shown for rightwards rotation of the drive shaft 2c. In this case, the ramp has in relation to the sensor 10k a rising form, with the consequence that positive potential pulses are generated.

In FIG. 14b there are shown the potential pulses in the case of leftwards rotation of the drive shaft. Since here the ramp has in relation to the sensor 10k a falling form, the potential pulses are negative.

In both figures the pulses have a temporal duration $t_1$ and a temporal separation $t_2$. The periodic duration is T. The relationship between the angle Φ shown in FIG. 13 and the times indicated in FIGS. 14a and 14b is provided by the formula:

$$\Phi = 360° * t_1/T$$

The speed of rotation n of the drive shaft 2c is n=1/T. Through measurement of $t_1$ and $t_2$ or T the coding angle Φ can be deduced.

By measurement of the amplitude of the potential U, with the knowledge of the speed of rotation n, the ramp form can be determined, which can thus be put to use also for coding.

The polarity of the potential pulses provides information concerning the direction of rotation (to the left or to the right) of the drive shaft 2c.

With the exemplary embodiment according to FIGS. 15 and 16 the coding 10a is in each case alterable. The coding 10a is not only able to make available certain data which is readable by the reading device 10b, but the coding 10a can be changed with regard to the data stored therein, and this with data which is transferred thereto from the electronic control device 13. Here there may be involved operational data, for example at least one operational program predetermined by the manufacturer or produced by the user. Other information may also be involved, for example information which relates to the operation of the instrument 2 and/or the patients to be treated and/or the treatment of the instrument in the sense of maintenance procedures. Thereby, the reading device 10b is at the same time a data transmitter and a receiver 10o and the coding 10a is alterable through a transfer of data from the data transmitter 10o and preferably constituted by means of a memory element 10p for the overwriting of its data with the data transferred from the data transmitter 10o. FIGS. 15 and 16 show by way of example two exemplary embodiments for such a data transfer device with which the data can be selectively transferred that is called up and again read in, both in the one and also the other direction between the electronic control device 13 and the memory element 10p.

FIG. 15 shows an exemplary embodiment having mechanical contact means 10q between the data receiver and transmitter 10o and the memory element 10p. The individual electrical contacts are, for reasons of simplicity, not illustrated. FIG. 16 shows a contact-less data transfer between the data receiver and transmitter 10o and the memory element 10p. The data transfer may be effected for example electromagnetically or inductively. The memory element 10p may be constituted by means of a transponder, namely a receiver-transmitter apparatus, which works in accordance with a query-response system. In the case of the data receiver and transmitter 10o there may be involved a corresponding transponder. In both cases there are involved memory elements which are in each case constituted by a prefabricated, in particular pin-like components and which are put in place in a recess, corresponding to the recesses 21, 22.

Due to the transfer to the instrument 2 of such data as is determinative for an intended working of the instrument 2 on the patient and/or for a treatment of the instrument 2 itself, for example maintenance measures, and/or for a registration of data, it is possible to combine the instrument 2 with another apparatus that has a data receiver or a reading device which receives this data and preferably can transfer back data to the memory element 10p. In the case of such a further apparatus there may involved for example a second working device (not illustrated) available to the user and/or a maintenance apparatus, which will be described below. Thereby, with the exemplary embodiments according to FIGS. 15 and 16 there is needed no data line directly between the supply apparatus 3 and the further apparatus, since the data carriage can be effected by means of the instrument 2.

With all above-described exemplary embodiments it is advantageous to arrange the sensitive components, here the reading device 10b, on the connection part 9 or on the coupling pin 8b projecting from this, and to arrange the coding on the instrument 2. Through this, the less sensitive parts of the identification device 10 are arranged on the instrument 2 which in the case of cleaning, disinfection and/or sterilisation is subject to significant demands, in particular temperatures. Beyond this, the electronic control device 13 is connected by means of at least one suitable data line with the reading device 10b or with the data receiver and transmitter 10o.

FIGS. 3 to 5 in each case show by way example such a second apparatus as a maintenance apparatus, wherein FIGS. 3 and 4 each show a sterilisation apparatus 31 and FIG. 5 shows a maintenance apparatus 32 for cleaning and oiling.

The sterilisation apparatus 31 according to FIG. 3 has, in a housing 33, a sterilisation chamber 34 which can be opened and closed by means of a non-illustrated door, so that an instrument 2 to be sterilised can be brought into and placed in the sterilisation chamber 34, for example on a repository or bowl 35. In order to be able to be used with instruments 2 in accordance with the above-described configurations according to FIGS. 6 to 11 and 15 and 16, there is associated with the sterilisation apparatus 31 a reading device 10b or a data receiver and transmitter 10o, which may be located within or outside the sterilisation chamber 34 and can identify the instrument 2 on the basis of the coding 10a and carries out the supply measures necessary for the disinfection, for which purpose there is included for example the heating of the sterilisation chamber 34 to the necessary sterilisation temperature, for example at least 135°, and if appropriate also the generation of an over-pressure or under-pressure in the sterilisation chamber 34. With the reference numbers 36 and 37 there are schematically associated a supply apparatus for making available the sterilisation media and an electronic control apparatus having an evaluation circuit for the read data and for controlling the sterilisation measures. The data read by the reading device 10b or by the data receiver 10o is delivered to the control device 37 for the purpose of recognition of the instrument 2 and control of the sterilisation measures.

The exemplary embodiment according to FIG. 4 differs from that according to FIG. 3 in that there is arranged in the sterilisation chamber 34 a coupling pin 8b1 corresponding in form and size to the coupling pin 8b, for example being attached to a wall of the sterilisation chamber 34, onto which the instrument 2 can be inserted with its coupling recess 8a. Also with this exemplary embodiment, the coupling 8 may be correspondingly oppositely formed; that is, there can be arranged in the sterilisation chamber a coupling recess into which an instrument 2 can be inserted with a projecting coupling pin. Through this there is provided in the sterilisation chamber 34 a positioning device for the instrument 2, which facilitates the positioning and recognition of the instrument 2 and the data.

The maintenance apparatus 32 according to FIG. 5 has, in a housing 38, a maintenance chamber 39 which can be selectively opened and closed by means of a non-illustrated door and into which the instrument 2 is brought and positioned in the maintenance chamber 32 for a maintenance procedure, for example on a repository or bowl or on a coupling part, in particular on a coupling pin 8b1 such as has already been described for the sterilisation apparatus 31. The maintenance apparatus 32 may have a plurality of coupling parts or coupling pins 8b1 for different instruments 2, as is schematically indicated in FIG. 5. Also the sterilisation apparatus 31 in accordance with FIGS. 3 and 4 may have a plurality of such coupling parts for different instruments 2. The maintenance apparatus 32 also has a supply apparatus 36 and an electronic control device 37 having an evaluation circuit for the read data for making available maintenance media, for example compressed air or a maintenance medium, in particular oil, and delivery of these media to the instrument 2 and for controlling these measures for the purposes of carrying out the cleaning and/or maintenance. The maintenance apparatus 32 can otherwise be of the kind described in the introduction.

As for the maintenance apparatus 31, the maintenance apparatus 32 also has in each case a reading device 10b or a data receiver and transmitter 10o associated with the coupling parts 8b1 belonging thereto, which recognise the introduced or coupled instrument 2 on the basis of a coding 10a or data storage and pass on the data to the control device 37 for controlling the supply apparatus 36 and for carrying out the maintenance measures.

In the first or second maintenance apparatus, here the sterilisation apparatus 31 and the maintenance apparatus 32 or an additional or other apparatus, there may be associated in each case a computer 14a, if applicable with screen 15, for the processing of the data concerned and for carrying out control corresponding to the data. Beyond this there can be associated with each of these apparatuses a registration device 16 for the registration of operational data and information, for example for the registration of the maintenance measures carried out, in particular the desired values and actual values of this operational data. Here, in the case of the sterilisation apparatus 31, there may be involved for example the sterilisation time and/or the sterilisation temperature and/or the sterilisation over-pressure or under-pressure. With the maintenance apparatus 32 there may be involved for example the maintenance or functioning time of maintenance measures such as through-blasting time, and/or oiling time and/or oil quantity.

In the case of the exemplary embodiment there are present, illustrated in a simplified manner, delivery lines 41 for the maintenance media, here compressed air and oil, which extend from the respectively associated reservoir to the coupling part or parts 8b1 and in the coupled condition of the instrument 2 stand in connection with the media channels of the instrument 2, here the channels 18, 19 and/or the one so-called drive channel in which the drive shaft of the instrument 2 is rotatably mounted, for the purpose of cleaning by means of a blasting through of compressed air and maintenance of the drive channel through the introduction or blasting in of maintenance media, in particular oil.

With a configuration in accordance with FIGS. 15 and 16 a direct networking of the apparatuses 1 and/or 31 and/or 32 by means of data lines 42 can be omitted, since the necessary data can be stored in the instrument 2 and transferred with the instrument 2 to the apparatus concerned or called up from the apparatus concerned. With the configurations in which the coding 10a can only be read by means of the reading device 10b, a networking 42 of the at least two apparatuses is necessary. The networking can be effected by means of specific electrical lines or in a wireless manner, for example via infrared or radio transmission paths. It is possible to equip the at least two apparatuses 1 and/or 31 and/or 32 and/or at least one further apparatus, for example a second working apparatus, with a common electronic control device 13 or with a common computer 14, a common registration device 16 and a common printer 17. With such a configuration a networking 42 is then also necessary if instruments 2 are to be maintained or treated in accordance with FIGS. 15 and 16 since the control is effected in common.

Below, diverse advantages and functions of the configurations in accordance with the invention will be described.

With the exemplary embodiment according to FIGS. 1 and 2, the working apparatus 1 forms, with a possibly present treatment chair, a treatment station, whereby there may be involved a surgical apparatus, in particular a microsurgical apparatus, or a dental treatment apparatus. As a result of the registration not only of the desired values but also of the actual values of operational data, for example the maximum torques or maximum tool speeds of rotation occurring upon use, and further operational information, such as for example the time or the date, the desired value and also the actual value of operational data can be called up not only during the working but also subsequently to the working and can be temporarily or permanently represented, for example on the screen 15 and by means of printing at the printer 17. Thus, the use of the instrument 2 in the working of the patient or body and/or the treatment of the instrument 2 itself, for example for the purpose of maintenance, can be determined and assessed, which in particular with regard to warranty claims and working life is of significance.

These advantages and measures apply not only for a treatment apparatus according to FIGS. 1 and 2 but also for a maintenance apparatus 32 for the carrying out of cleaning and/or disinfection and/or sterilisation measures.

The configurations in accordance with the invention make possible the recognition and fulfilment of the following requirements of the instrument or instruments 2.

a) Which instrument 2 is involved?

b) What requirements does the instrument 2 present? For example, operational data such as speed of rotation, torque; which operating medium (air, water, electrical current etc.) is necessary?

c) In what condition is the instrument? For example how many hours of operation has the instrument already run for; is the instrument 2 clean or disinfected or sterilised or maintained?

The requirements a) and b) are recognised by the individual or common electronic control device in each case by means of comparison and evaluation of the recognised identification data with the data stored in the electronic control device. The requirement c) is fulfilled in that the operational data concerned is determined and registered and thus the registered data concerned represents the current condition of the instrument 2. Through a continuing registration of data there can also be registered the operational development and thus not only particular operational functions of working and of maintenance. Specific operational procedures or data can be so controlled in dependence upon previous operational procedures or stored data that a certain operational procedure can only be affected if a previous operational procedure has taken place or a particular operational condition has been attained, which is registered or stored by means of data. If for example an instrument 2 has not been maintained, the control device recognises this defect on the basis of the lack of relevant data and it blocks the subsequent operational procedure or indicates this fault by means of a warning signal or registers this fault. If for example an instrument 2 has not been maintained or has been insufficiently maintained, if for example the sterilisation temperature and/or sterilisation time do not correspond to the desired value, the control device recognises this at the latest upon coupling of the instruments to the supply apparatus 3, whereby the control device can block the use or at least indicate the fault.

Such a blocking or indication can also be controlled if the instrument 2 has exceeded a predetermined number of operating hours, which can likewise be monitored by means of the registration of associated data.

The invention is based upon the insight that operational procedures and conditions of at least one instrument 2 can be recognised at at least two working and/or supply apparatuses, when the apparatuses and/or the instruments are stored with appropriate recognition data. An instrument 2 is for example coupled with a maintenance apparatus 31 or 32 for its maintenance. This apparatus recognises the respective kind of the instrument. The apparatus now calls up the stored data for exactly this instrument 2. In accordance with these parameters (oil quantity, blasting out time) the maintenance cycle is started. After completed maintenance, there are stored associated procedural or maintenance data, for which purpose also the serial number of the instrument 2 may serve.

When also at least one other apparatus is in a position to call up and to store the data of the preceding operational procedure, one can through the data networking of the apparatuses follow up operational procedures of a plurality of apparatuses, for example the maintenance and working of the instrument 2.

For example, instrument A was subject to maintenance in maintenance apparatus 32 on Jan. 16, 2001 at 10.00 hours. Instrument A was sterilised in sterilisation apparatus 31 on Jan. 16, 2001 at 10.05 hours. Instrument A was operated for a total of 5 minutes on working apparatus 1 (patient 4) on Oct. 16, 2001 at 11.00 hours. Through this not only the operational procedure can be determined but also faults can be determined for example by means of a fault report which the associated control device derives or recognises upon coupling of the non-sterilised instrument 2.

The invention claimed is:

1. Medical or dental-medical instrument having a memory element for storing data such as identification, date, and/or operational parameter data,
   wherein the memory element is capable of overwriting the data by other data,
   and wherein the instrument has a coupling part with which it can be coupled to a corresponding coupling part of a supply line of a supply apparatus for the supply of the instrument with media, a sterilization apparatus, and a maintenance apparatus,
   wherein, the coupling part is formed by means of coupling recess arranged rearwardly on the instrument or a coupling pin standing up rearwardly from the instrument, and
   wherein the memory element is arranged in a sleeve wall surrounding the coupling recess and is accessible for the corresponding coupling part from a inner surface of the sleeve wall or from a rearward annular end surface of the ring wall,
   or is arranged in the coupling pin and is accessible from a surface of the coupling pin or is arranged in a base of the coupling pin behind an annular step surface and is accessible from the annular step surface.

2. Instrument according to claim 1, wherein the memory element comprises contact means for taking up and/or issuing data.

3. Instrument according to claim 1, wherein the memory element comprises means for taking up and/or issuing data without contact.

4. Use of an instrument according to claim 1, wherein this instrument passes through at least one working phase and at least one maintenance phase, wherein there is written into the memory element at least one parameter from the working phase and this working phase parameter is read out for control of the maintenance phase, and/or there is written into the memory element at least one parameter of the maintenance phase and this maintenance phase parameter is read out for control of the working phase.

5. Supply apparatus for supplying media to at least one medical or dental-medical instrument according to claim 1, wherein the supply apparatus is computer-controlled and there extends from the supply apparatus a supply line at an end of which there is arranged a coupling part with which the supply line can be connected with the instrument, and wherein in the region of the coupling part there is arranged a data receiver for the reception of identification date and/or operational data which is stored in a memory element of the instrument,
   wherein the coupling part is formed by a coupling pin projecting from the supply line and the data receiver or transmitter is arranged either in the coupling pin or behind an annular shoulder surface from which the coupling pin extends.

6. Supply apparatus according to claim 5, wherein the data receiver is also a data transmitter for the transfer of data to the memory element.

7. Maintenance apparatus for at least one medical or dental-medical instrument according to claim 1, wherein the maintenance apparatus has a coupling part by means of which the instrument can be coupled with the maintenance apparatus,
   wherein the coupling part is formed by a projecting coupling pin and a reading device for reading out of identification data and/or operational parameter data stored in the instrument is arranged either in the coupling pin or behind an annular shoulder surface from which the coupling pin extends.

8. Instrument according to claim 1, wherein the coupling part in which the memory element is arranged is integral with the medical or dental-medical instrument.

9. System for working and maintenance of a medical or dental-medical instrument, having a supply apparatus from which the instrument is supplied with media for working, and having a maintenance apparatus, for maintenance of the instrument, wherein the supply apparatus is connected with a computer that stands in data exchange with the supply apparatus, wherein the maintenance apparatus is also connected with the computer and stands in data exchange therewith, and both the supply apparatus and also the maintenance apparatus have a reading device for the reading out of identification and/or operational parameter data stored in the instrument;

wherein both the supply apparatus and the maintenance apparatus each have a coupling part with which the instrument can be coupled, wherein each reading device is arranged in the region of the respective coupling part.

10. System according to claim 9, wherein each coupling part is formed by a projecting coupling pin and each reading device is arranged in the respective coupling pin or behind an annular step surface from which the coupling pin projects.

11. System for at least one medical or dental-medical instrument capable of going through operational phases on at least two apparatuses, comprising:

a sterilization apparatus and a maintenance apparatus each selectively couplable to the medical or dental-medical instrument, registration means in communication with the sterilization apparatus and the maintenance apparatus that register the progression or a desired value and/or actual value of operational data of at least one operational phase of both the sterilization apparatus and the maintenance apparatus.

12. System according to claim 11, wherein a fault report takes place and/or an operational phase is blocked at an apparatus if a previous operational phase has not been run through or an actual value of the data of a previous operational phase is missing or is not compliant.

* * * * *